United States Patent [19]
Gries et al.

[11] Patent Number: 5,683,708
[45] Date of Patent: Nov. 4, 1997

[54] **COMPOSITION OF CHEMICALS FOR MANIPULATING THE BEHAVIOR OF NUN MOTH, *LYMANTRIA MONACHA* (L.), AND GYPSY MOTH, *LYMANTRIA DISPAR* (L.)**

[75] Inventors: Gerhard Gries, Coquitlam; Gary Grant, Sault Ste. Marie; Grigori Khaskin, Port Moody; Regine Gries, Coquitlam; Keith N. Slessor, Maple Ridge, all of Canada; Jan Liska; Petr Kapitola, both of Praha, Czechoslovakia

[73] Assignee: Simon Fraser University, Burnaby, Canada

[21] Appl. No.: 536,785

[22] Filed: Sep. 29, 1995

[51] Int. Cl.$^6$ .................... A01N 25/08; A01N 27/00; A01N 31/02

[52] U.S. Cl. .................... 424/408; 424/405; 424/84; 514/475; 514/762; 514/919

[58] Field of Search .................... 424/405, 408, 424/84; 574/475, 762, 919

[56] References Cited

U.S. PATENT DOCUMENTS 3,629,072  12/1971  Casida et al. .................... 195/28
5,342,618  8/1994  Leonhardt et al. .................... 464/409

OTHER PUBLICATIONS

Kost et al. Bioorg. Khim. (1977), 3(7), 934–42 Synthesis & Biological Activity of Disparture With Analogs.

Oldinov et al Insect Phenomones (:Highly Selective Synthesis of (Z)–disparture a Racemic Analog of the Sex Phenomone of Polthetria Dispar Khim. Prir. Saedin. (1995), (6), 901–904.

Guelz et al. Z. Pflanzenphyonol. (1978), 89(2), 159–67 Hydrocarbons of the Blue Green Algae Lichen Antisera Cancer (L).

Jensen, T.S., et al., "Evaluation of pheromone catches of the nun moth, *Lymantria monacha* L.", B.O.J. Appl. Entomol. 98, 399–413 (1984).

Schönherr, J., "Nun moth outbreak in Poland 1978–1984", J. Appl. Entomol. 99, 73–76 (1984).

Bejer, B., "The Nun Moth in European Spruce Forests", In Dynamics of forest insect populations: Patterns, causes, implications (ed. Berryman, A.), Plenum Publ. Corp., New York, U.S.A., 603 pp. (1988).

Grjpma, P., "Overview of Research on Lymantrids in Eastern and Western Europe", In Proceedings, Lymantriidae: a comparison of features of new and old world tussock moths Dept. of Agr., Forest Service, Northeastern Forest Experiment Station, Gen. Tech. Rep. NE–123, 554 pp. (1988).

Sliwa, E., et al., "Gradation der Nonne (*Lymantria monacha* L.) in Polen von 1978 bis 1984", Z. Anz. Schädlingskde, Pflanzenschutz, Umweltschutz 59, 81–86 (1986).

Majunke, C., et al., Forstwirts. 19, 89–91 (1985).

Skuhravy, V., "A review of research on the nun moth (*Lymantria monacha* L.) conducted with pheromone traps in Czechoslovakia, 1973–1984", Anz. Schädlingsk. Pflanzensch, Umweltschutz 60, 96–98.

(List continued on next page.)

*Primary Examiner*—Neil S. Levy
*Attorney, Agent, or Firm*—Oyen Wiggs Green & Mutala

[57] ABSTRACT

This invention relates to a composition and procedure for manipulating the behaviour of nun moth, *Lymantria monacha* (L.) and gypsy moth, *Lymantria dispar* (L.). More particularly, this invention relates to the preparation and use of chiral and racemic disparlure, chiral or racemic cis-7,8-epoxy-octadecane, 2-methyl-Z7-octadecene and Z7-octadene for manipulating the behaviour of nun moth and gypsy moth. A composition of chemicals for manipulating the behavior of nun moth and/or gypsy moth, said composition comprising two or more chemicals selected from the group consisting of: (a) 2-methyl-7R,8S-epoxy-octadecane (RS-disparlure); (b) 2-methyl-7S,8R-epoxy-octadecane (SR-disparlure); (c) 7R,8S-epoxy-octadecane; (d) 7S,8R-epoxy-octadecane; (e) 2-methyl-Z7-octadecene; and (f) Z7-octadecene.

14 Claims, 6 Drawing Sheets

OTHER PUBLICATIONS

Bierl, B.A., et al., "The Presence of Disparlure, the Sex Pheromone of the Gypsy Moth, in the Female Nun Moth", Naturforsch. 30c, 672–675 (1975).

Skatulla, U., Anz. Schädlingskde., Pflanzenschutz, Umweltschutz 62, 50–53 (1989).

Jensen, T.S., "Integrated pest management of the nun moth, *Lymantria monacha* (Lepidoptera: Lymantriidae) in Denmark", Forest Ecol. and Manage., 39, 29–34 (1991).

Krehan, H., Forstschutz–Aktuell 14, 1–2 (1994).

Mason, R.R., "Monitoring Population Change in the Lymantriidae", In Proceedings, Lymantriidae: a comparison of features of new and old world tussock moths, Dept. of Agr. Forest Service, Northeastern Forest Experiment Station, Gen. Tech. Rep. NE–123, 554 pp. (1988).

Jensen, T.S., "Registration and control of the nun moth *Lymantria monacha* L.", Mitt. Dtsch. Ges. Alg. Angew. Entomol. 4, 146–149 (1984).

Zdarek, J., et al., "Male Confusion of the Nun Moth with Disparlure at High and Low Population Densities", J. Chem. Ecol. 14:537–547 (1988).

Bierl, B.A., et al., "Potent Sex Attractant of the Gypsy Moth: Its Isolation, Identification and Synthesis", Science 170, 87–89 (1970).

Bierl, B.A., "Isolation, Identification and Synthesis of the Gypsy Moth Sex Attractant", J. Econ. Entomol. 65, 659–664 (1972).

Hansen, K., "Discrimination and production of disparlure enantiomers by the gypsy moth and the nun moth", Physiol. Entomol. 9, 9–18 (1984).

Vité, J.P., et al., "Chirality of Insect Pheromones: Response Interruption by Inactive Antipodes", Naturwissenschaften 63, 582–583 (1976).

Miller, R.J., et al., "Gypsy Moth Field Trapping and Electroantennogram Studies with Pheromone Enantiomers", Insect Physiol. 23, 1447–1453 (1977).

Cardé, R.T., et al., "Attractancy of Racemic Disparlure and Certain Analogues to Male Gypsy Moths and the Effect of Trap Placement", Environ. Entomol. 6, 765–767 (1977).

Plimmer, J.R., et al.; "Contrasting Effectiveness of (+) and (–) Enantiomers of Disparlure for Trapping Native Populations of Gypsy Moth in Massachusetts", Environ. Entomol. 6, 518–522 (1977).

Cardé, R.T., et al., "Attractancy of Optically Active Pheromone for Male Gypsy Moths", Environ. Entomol. 6, 768–772 (1977).

Cardé, R.T., et al., "Natural Inhibitor of the Gypsy Moth Sex Attractant", Nature 241, 474–475 (1973).

Arn, H. et al., "The Electroantennographic Detector—a Selective and Sensitive Tool in the Gas Chromatographic Analysis of Insect Pheromones", Naturforsch. 30c, 722–725 (1975).

COMPOSITION OF CHEMICALS FOR MANIPULATING THE BEHAVIOR OF NUN MOTH, *LYMANTRIA MONACHA* (L.), AND GYPSY MOTH, *LYMANTRIA DISPAR* (L.)

FIELD OF THE INVENTION

This invention relates to a composition and procedure for manipulating the behaviour of nun moth, *Lymantria monacha* (L.), and gypsy moth, *Lymantria dispar* (L.). More particularly, this invention relates to the preparation and use of chiral and racemic disparlure, chiral or racemic cis-7,8-epoxy-octadecane, 2-methyl-Z7-octadecene and Z7-octadecene for manipulating the behaviour of nun moth and gypsy moths.

BACKGROUND OF THE INVENTION

Nun moth, *Lymantria monacha* (L.) (NM), occurs in Central and Eastern Europe and isolated areas in Asia. Spreading widely, it reached the Ukraine in 1949–1952, and central European Russia and western Siberia in 1954–1957 (1). In northern and north-western Europe its distribution is limited to South England, Norway, Denmark, Sweden and Finland. In southern Europe, NM is present in Portugal, northern Spain, Croatia, Italy, Yugoslavia, Greece and Bulgaria. NM is one of the most important forest pests in Europe (2, 3). Although it is considered the classic insect pest of spruce forests (3), it also defoliates coniferous hosts belonging to the genera Picea, Pinus, Larix, and Abies. Of deciduous trees, Carpinus, Betula, Quercus, Alnus and Acer be attacked (4).

Previous NM outbreaks exemplify the economic impact of this defoliator in Europe, and demonstrate the tremendous threat to North America's forest industry, if NM were introduced and became established in the new world. In 1853–1863, for example, 403,000 $km^2$ (about 155,000 square miles) of (now) Poland–Russia were damaged or destroyed (4).

During the massive outbreak in Poland in 1978–1984, 6.3 million ha of coniferous and mixed stands were affected (5), and in Eastern Germany in 1983 and 1984, extensive countermeasures were necessary to control a NM outbreak on more than 300,000 ha of forest land (6).

Methods for monitoring and forecasting NM epidemics have been based upon larval frass droppings and counts per tree of larvae, pupae, adults and eggs (7). Monitoring of NM using the sex pheromone of live females started as early as 1932 in Czechoslovakia (8). With the identification of a NM sex pheromone component, 2-methyl-cis-7,8-epoxy-octadecane (disparlure) (9), efforts are ongoing to correlate catches of NM males in pheromone-baited traps with NM population densities (2, 10, 11, 12, 13). NM populations are currently monitored by pheromone traps in many parts of Europe (14).

Pheromones have also been considered for post-outbreak control of NM through mating disruption. In 1980 and 1982 in Denmark, pheromone traps placed in areas aprayed with microencapsulated disparlure caught no NM males, whereas traps in control areas attracted large number of males (15). Moreover, 10–20 g of disparlure/ha dispensed per flight season successfully disoriented NM males in stands of low NM population densities (16).

There is, however, evidence that disparlure is not the only NM sex pheromone component, and that the efficacy (species-specificity) of pheromone-based monitoring and/or control of NM populations could be improved. Sympatric and co-seasonal gypsy moth (GM), *Lymantria dispar* (L.), also utilizes disparlure as a pheromone component (17, 18). Even though female GM may emit only 7R,8S-disparlure and female NM may emit both 7R,8S-(10%) and 7S,8R-(90%)-disparlure (19), inhibitory characteristics of the SR-enantiomer do not entirely prevent cross attraction of GM males to racemic RS- plus SR-disparlure baited traps (20–25). Moreover, increasing the amount of the olefin precursor of disparlure, 2-methyl-Z7-octadecene, in disparlure baits progressively reduced attraction of GM males and prompted Grant et al. to test the olefin as a candidate pheromone component for NM (26). Finally, pheromone communication of GM during the day and of NM at night contributes to reproductive isolation, but mate seeking males of both species are encountered at sunset (27). This overlap in diurnal flight periodicity suggested additional as yet unidentified sex pheromone components in both moths which could impart specificity to their chemical communication. For example, in competitive tests, NM females were more effective than GM females in attracting NM males (9 plus references therein).

Previous patents related to the capture, monitoring or control of GM adults comprise: (1) treatment of female GM abdominal tips with a solution of m-chloro-perbenzoic acid (28); (2) the preparation (synthesis) of disparlure (29,30); (3) a dispenser for release of (+)-disparlure (31); (4) a sprayable adhesive for GM pheromone beads (32); and (5) various trap types (33,34,35,36). This document describes the multiple component NM pheromone blend and reveals the compounds that inhibit cross-attraction of congeneric GM. Because NM and GM males captured in monitoring traps quickly loose their characteristic body and wing scales, and because NM occurs in many color morphs, which are not recognized by non-experienced personal, species-specific lures become extremely valuable and important.

SUMMARY OF THE INVENTION

Gas chromatographic-electroantennographic detection (GC-EAD) analyses of female nun moth (NM), *Lymantria monacha* (L.), pheromone gland extract revealed 5 antennally active compounds. They were identified as: 1) Z7-octadecene; 2) 2-methyl-Z7-octadecene; 3) cis-7,8-epoxy-octadecane, 4) 2-methyl-cis-7,8-epoxy-octadecane (previously known as disparlure), and 5) cis-7,8-epoxy-nonadecane. In field experiments near Zbraslav, Czech Republic, a ternary combination of 2-methyl-7R,8S-epoxy-octadecane (7R,8S-disparlure), 2-methyl-Z7-octadecene and 7R,8S-epoxy-octadecane at a 10:1:10 ratio was most effective in attracting NM males. Antipodes of 7R,8S-disparlure and of 7R,8S-epoxy-octadecane neither enhanced nor reduced attractiveness of the lure for NM males. Cross attraction of gypsy moth (GM), *Lymantria dispar* (L.), males was reduced by each of 7S,8R-disparlure, 7R,8S-epoxy-octadecane, 7S,8R-epoxy-octadecane, 2-methyl-Z7-octadecene, and Z7-octadecene, but these compounds in combinations were most inhibitory to GM. The essence of the invention is the preparation and use of chiral and racemic disparlure, chiral or racemic cis-7,8-epoxy-octadecane and 2-methyl-Z7-octadecene for manipulating the behavior of NM and GM.

The invention is directed to a composition of chemicals for manipulating the behavior of nun moth and/or gypsy moth, said composition comprising [two or more chemicals selected from the group consisting of: (a)] 2-methyl-7R,8S-epoxy-octadecane (RS-disparlure); [(b)] 2-methyl-7S,8R-epoxy-octadecane (SR-disparlure); and 2-methyl-Z7-octadecene plus one or more chemicals selected from the group consisting of [(c)] (a) 7R,8S-epoxy-octadecane; [(d)] (b) 7S,8R-epoxy-octadecane; [(e) 2-methyl-Z7-octadecane;] and [(f)] (c). Z7-octadecene.

The chemicals in the composition can comprise 7R,8S-disparlure and 7R,8S-epoxy-octadecane. The chemicals can comprise 7R,8S-disparlure and 2-methyl-Z7-octadecene. The chemicals can comprise 7R,8S-disparlure, 7R,8S-epoxy-decane and 2-methyl-Z7-octadecene. The chemicals can comprise 7R,8S-disparlure, 7S,8R-disparlure and 7R,8S-epoxy-octadecane. The chemicals can comprise 7R,8S-disparlure, 7R,8S-disparlure, 7R,8S-epoxy-octadecane and 7S,8R-epoxy-octadecane. The chemicals can comprise 7R,8S-disparlure, 7S,8R-disparlure and 2-methyl-Z7-octadecene. The chemicals can comprise 7R,8S-disparlure, 7S,8R-disparlure, 7R,8S-epoxy-octadecane and 2-methyl-Z7-octadecene. The chemicals can comprise 7E,8S-disparlure, 7S,8R-disparlure, 7R,8S-epoxy-octadecane, 7S,8R-epoxy-octadecane and 2-methyl-Z7-octadecane. The chemicals can comprise 7R,8S-disparlure, 7S,8R-disparlure, 7R,8S-epoxy-octadecane, 7S,8R-epoxy-octadecane, 2-methyl-Z7-octadecene and Z7-octadecene.

The chemicals' proportions can cover all possible combinations and ratios. The composition can be contained in, and released from, a trap that captures attracted nun moths or gypsy moths. The chemicals can be contained in, and released from, slow release devices.

The invention is also directed to a method of capturing nun moths and gypsy moths which comprises baiting a trap with two or more chemicals of the invention. The chemicals can be held in a slow release device.

DRAWINGS

In drawings which illustrate specific embodiments of the invention, but which should not be construed as restricting the spirit or scope of the invention in any way.

DETAILED DESCRIPTION OF INVENTION

Analysis of *L. monacha* Sex Pheromone Gland Extract

Female NM pupae were collected in spruce forests near Prague, Czech Republic, and were placed into translucent plastic containers with screened lids and kept outdoors at natural photoperiodic and temperature conditions. Two to four hours into the scotophase, pheromone glands of calling one to two-day old virgin females were removed and extracted for 5–20 minutes in hexane. NM males were laboratory-reared at the Forestry and Game Management Institute (Zbraslav) and shipped to Simon Fraser University for use in pheromone analyses. Analyzing aliquots of one female equivalent (37) of pheromone gland extract by GC with both flame ionization (FID) and electroantennographic detection (EAD: male NM or GM antennae) revealed four EAD-active compounds, of which only disparlure was FID-detectable (FIG. 1).

Figure 1:
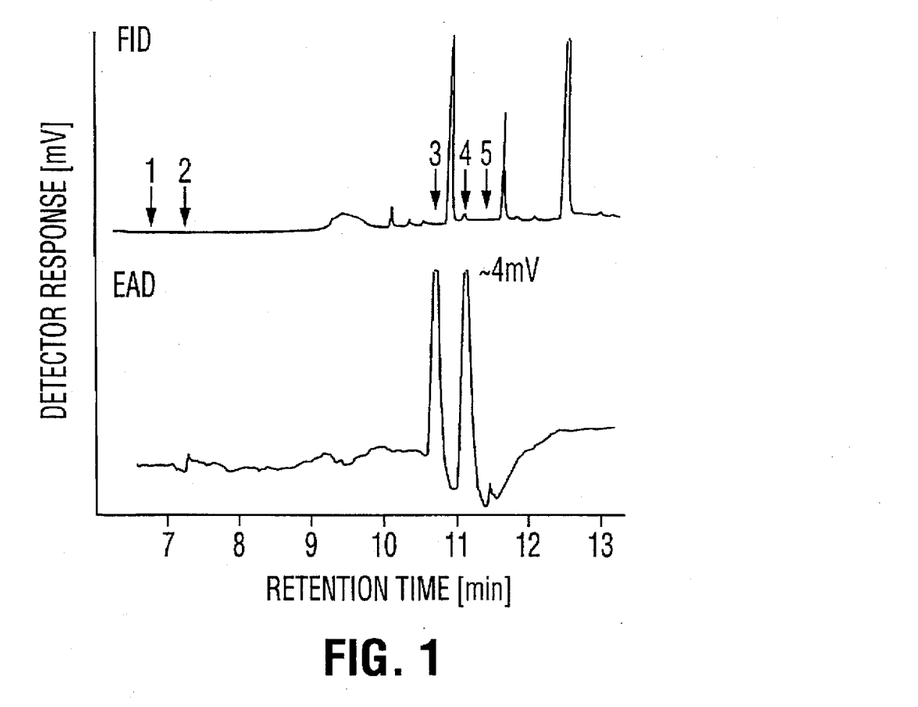
FIG. 1 illustrates flame ionization detector (FID) and electroantennographic detector (EAD: male *L. monacha* antenna) responses to one female equivalent of female *L. monacha* pheromone gland extract.

FIG. 1 illustrates flame ionization detector (FID) and electroantennographic detector (EAD: male *L. monacha* antenna) responses to one female equivalent of female *L. monacha* pheromone gland extract. EAD-active compound 1 (antennal response not visible in the depicted trace) 2, 3, 4 and 5 were identified as Z7-octadecene [Z7-18Hy]; 2-methyl-Z7-octadecene [2-me-Z7-18Hy]; 7R,8S-(and/or 7S,8R)-epoxy-octadecane [7R,8S-(and/or 7S,8R)-epoxy-18Hy]; 2-methyl-7R,8S-(and/or 7S,8R)-epoxy-octadecane [7R,8S-(and/or 7S,8R)-disparlure] and 7R,8S-(and/or 7S,8R)-epoxy-nonadecane [7R,8S-(and/or 7S,8R)-epoxy-19Hy]. Only disparlure was previously known as an attractive sex pheromone component in *L. monacha* (9). Chromatography: DB-23 column; splitless injection, temperature of injection port: 220° C. and of the FID: 250° C.; temperature program: 100° C. (1 min) −10° C./min to 200° C.

Based on their retention indices, EAD-active compounds 1, 2, 3 and 5 were hypothesized to be Z7-octadecene, 2-methyl-Z7-octadecene, cis-7,8-epoxy-octadecane and homologous 7,8-epoxy-nonadecane. Rational syntheses of these compounds (38) and their analyses by GC-EAD (39) at quantities equivalent to pheromone gland extracts resulted in retention times of antennal responses identical for female-produced and synthetic components, confirming structural assignments. Synthetic 7R,8S-epoxy-octadecane, 7R,8S-disparlure and 7R,8S-epoxy-nonadecane elicited antennal responses significantly exceeding those to their antipodes.

Attraction of *L. monacha* males to Synthetic Test Chemicals

Experiments were conducted in mature spruce or oak forests near Zbraslav, Czech Republic. For each experiment, Delta traps (40) were suspended 1.5 m above ground from trees in randomized complete blocks with traps and blocks at 20–25 m intervals. Traps were baited with rubber septa (41) impregnated with test chemicals in HPLC grade hexane.

EXAMPLE #1

Figure 2:
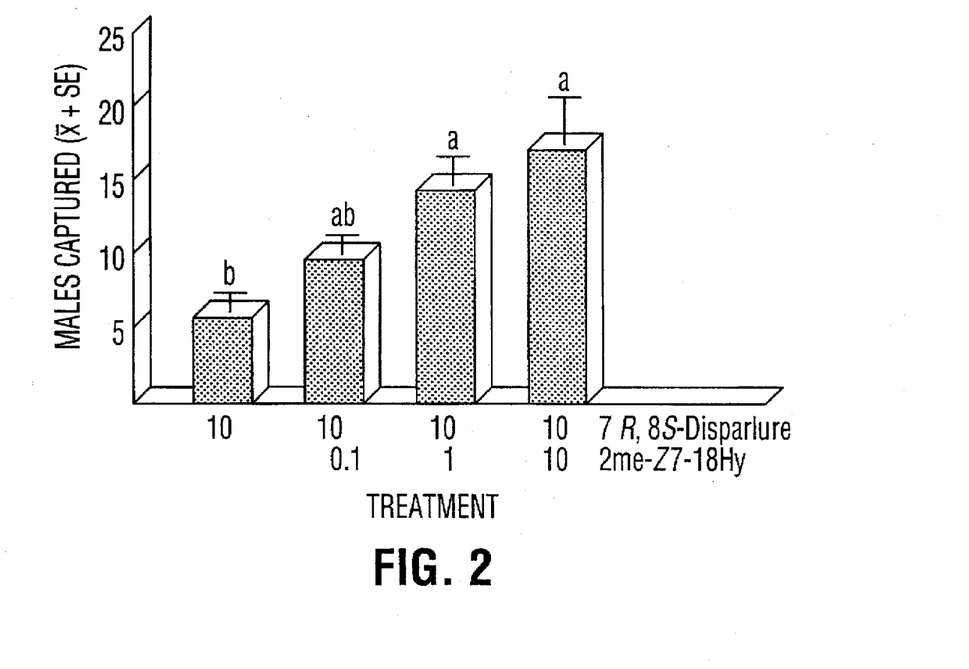
FIG. 2 illustrates graphical data of captures of *L. monacha* males in traps baited with 7R,8S-disparlure alone (10 µg) or in combination with 2-methyl-Z7-octadecene (2 me-Z7-18 Hy) at increasing proportions (0.1, 1 or 10 µg).

In a 4-treatment, 10-replicate experiment, attractiveness of 7R,8S-disparlure (10 µg) to NM males increased with increasing proportions (0.1, 1 or 10 µg) of 2-methyl-Z7-octadecene (FIG. 2). FIG. 2 illustrates graphical data of captures of *L. monacha* males in traps baited with 7R,8S-disparlure alone (10 µg) or in combination with 2-methyl-Z7-octadecene (2 me-Z7-18Hy) at increasing proportions (0.1, 1 or 10 µg). Spruce forest near Zbraslav, Czech Republic, 22–23 Jul., 1995; 10 replicates. Bars superscripted by the same letter are not significantly different; ANOVA on data transformed by log 10 (x+1) followed by comparison of means (Student-Newman-Keuls test) (42), $P<0.05$.

EXAMPLE #2

Figure 3:
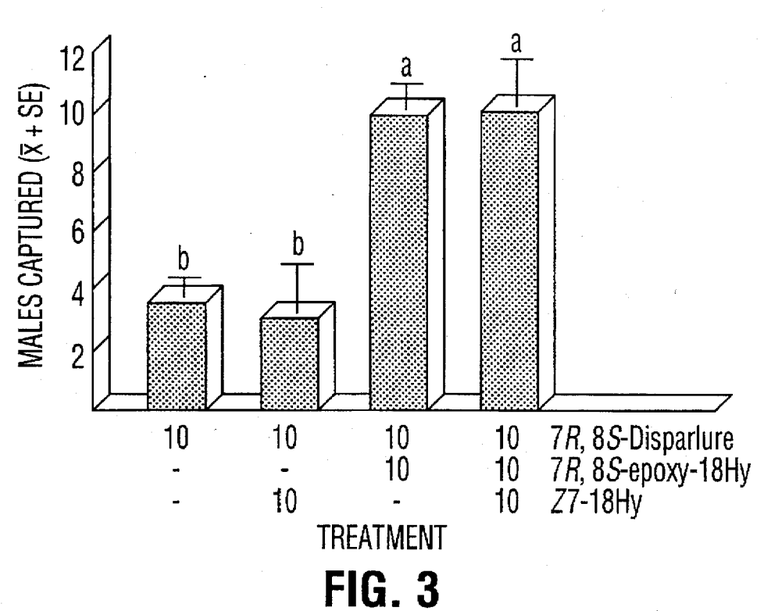
FIG. 3 illustrates graphical data of captures of *L. monacha* males in traps baited with 7R,8S-disparlure (10 µg) alone or in binary and ternary combinations with 7R,8S-epoxy-18Hy (10 µg) and Z7-18Hy (10 µg).

7R,8S-Disparlure (10 µg) in binary combination with 7R,8S-epoxy-octadecane (10 µg) was significantly more attractive to NM males than 7R,8S-disparlure alone (FIG. 3). FIG. 3 illustrates graphical data of captures of *L. monacha* males in traps baited with 7R,8S-disparlure (10 µg) alone or in binary and ternary combinations with 7R,8S-epoxy-18Hy (10 µg) and Z7-18Hy (10 µg). Spruce forest near Zbraslav, Czech Republic, 24–26 Jul., 1995; 20 replicates. Bars superscripted by the same letter are not significantly different; nonparametric analysis of variance by ranks (Friedman's test) followed by comparison of means (Student-Newman-Keuls test) (42), $P<0.05$. Compound abbreviations as in FIG. 1.

EXAMPLE #3

Figure 4:
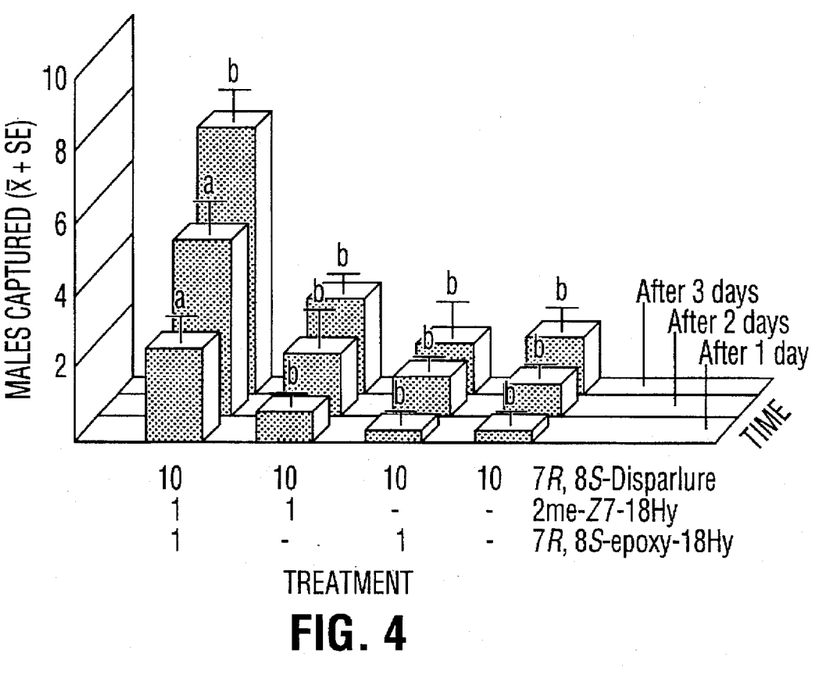
FIG. 4 illustrates graphical data of cumulative captures of *L. monacha* males in traps baited with 7R,8S-disparlure (10 µg) alone or in binary and ternary combinations with 2me-Z7-18Hy (1 µg) and 7R,8S-epoxy-18Hy (1 µg).

7R,8S-Disparlure (10 µg) in ternary combination with 2-methyl-Z7-octadecene (1 µg) and 7R,8S-epoxy-octadecane (1 µg) was significantly more attractive to NM males than 7R,8S-disparlure alone or than binary combinations of disparlure with either of these compounds (FIG. 4). FIG. 4 illustrates graphical data of cumulative captures of *L. monacha* males in traps baited with 7R,8S-disparlure (10 µg) alone or in binary and ternary combinations with 2me-Z7-18Hy (1 µg) and 7R,8S-epoxy-18Hy (1 µg). Oak forest near Zbraslav, Czech Republic, 25–28 Jul., 1995; 10 replicates. Bars in each horizontal row superscripted by the same letter are not significantly different; nonparametric analysis of variance by ranks (Friedman's test) followed by comparison of means (Student-Newman-Keuls test) (42); $<0.05$. Compound abbreviations as in FIG. 1.

EXAMPLE #4

Figure 5:
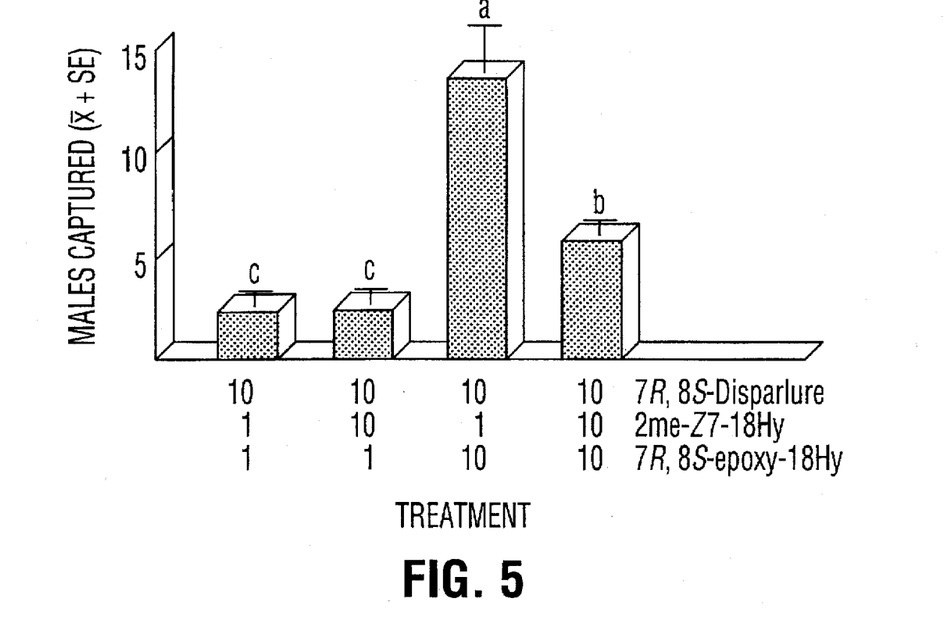
FIG. 5 illustrates graphical data of captures of *L. monacha* males in traps baited with ternary blends of 7R,8S-disparlure (10 µg), 2me-Z7-18Hy (1 of 10 µg) and 7R,8S-epoxy-18Hy (1 or 10 µg).

The blend of 7R,8S-disparlure, 2-methyl-Z7-octadecene and 7R,8S-epoxy-octadecane at a 10:1:10 ratio (µg) was significantly more attractive to NM males than ternary blends of these compounds at different ratios (FIG. 5). FIG. 5 illustrates graphical data of captures of *L. monacha* males in traps baited with ternary blends of 7R,8S-disparlure (10 µg), 2me-Z7-18Hy (1 or 10 µg) and 7R,8S-epoxy-18Hy (1 or 10 µg). Spruce forest near Zbraslav, Czech Republic, 30–31 Jul., 1995; 10 replicates. Bars superscripted by the same letter are not significantly different; ANOVA on data transformed by log 10 (x+1) (42); $P<0.05$. Compound abbreviations as in FIG. 1.

EXAMPLE #5

Figure 6:
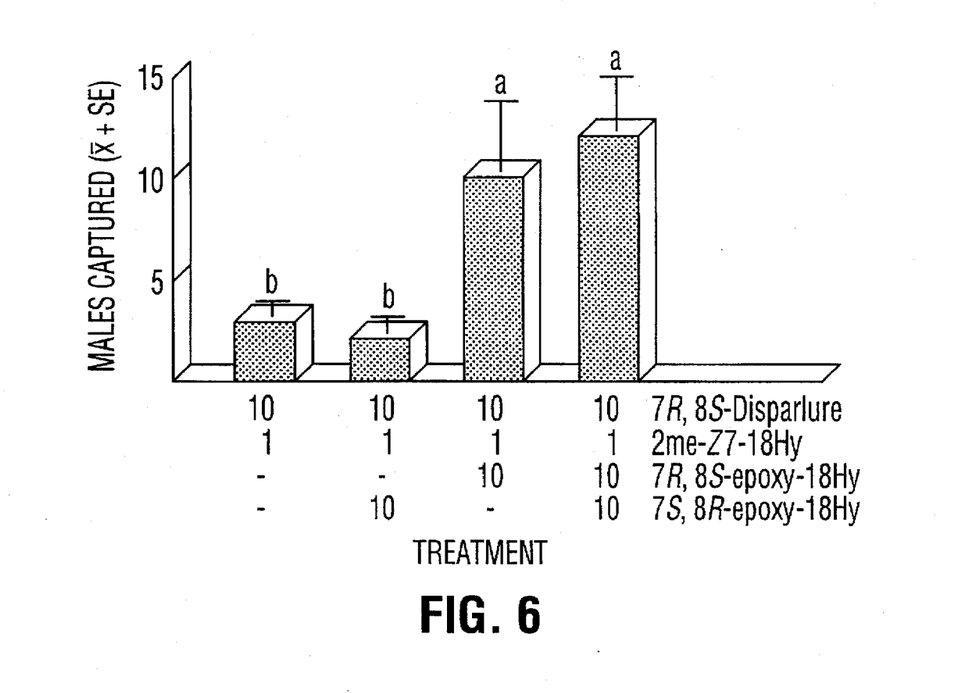
FIG. 6 illustrates graphical data of captures of *L. monacha* males in traps baited with 7R,8S-disparlure (10 µg) and 2me-Z7-18Hy (1 µg) plus either 7R,8S-epoxy-18Hy (10 µg), 7S,8R-epoxy-18Hy (10 µg) or both (10 µg each).

7R,8S-Epoxy-octadecane (10 µg), but not its antipode (10 µg) enhanced attractiveness of 7R,8S-disparlure (10 µg) plus 2-methyl-Z7-octadecene (1 µg) to NM males (FIG. 6). FIG. 6 illustrates graphical data of captures of *L. monacha* males in traps baited with 7R,8S-disparlure (10 µg) and 2me-Z7-18Hy (1 µg) plus either 7R,8S-epoxy-18Hy (10 µg), 7S,8R-epoxy-18Hy (10 µg) or both (10 µg each). Spruce forest near Zbraslav, Czech Republic, 2–3 Aug., 1995; 10 replicates. Bars superscripted by the same letter are not significantly different; ANOVA on data transformed by log 10 (x+1) followed by comparison of means (Student-Newman-Keuls test) (42), $P<0.05$. Compound abbreviations as in FIG. 1.

EXAMPLE #6

Figure 7:
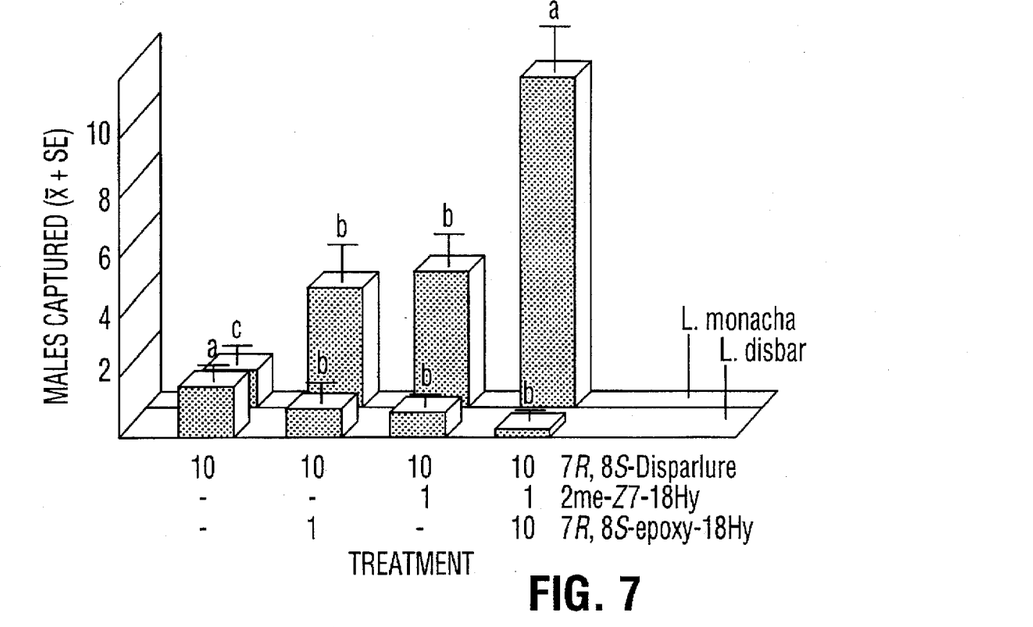
FIG. 7 illustrates graphical data of captures of *L. monacha* and *L. dispar* males in traps baited with 7R,8S-disparlure (10 µg) alone and in binary and ternary combination with 2me-Z7-18Hy (1 µg) and 7R,8S-epoxy-18Hy (1 µg).

Superior attractiveness to NM males of 7R,8S-disparlure in ternary combination with 2-methyl-Z7-octadecene (1 µg) and 7R,8S-epoxy-octadecane (10 µg) was confirmed in a final NM experiment (FIG. 7). FIG. 7 illustrates graphical data of captures of *L. monacha* and *L. dispar* males in traps baited with 7R,8S-disparlure (10 µg) alone and in binary and ternary combination with 2me-Z7-18Hy (1 µg) and 7R,8S-epoxy-18Hy (10 µg). Spruce forest near Zbraslav, Czech Republic, 2–4 Aug., 1995; 10 replicates. Bars in each horizontal row superscripted by the same letter are not significantly different; nonparametric analysis of variance by ranks (Friedman's test) followed by comparison of means (Student-Newman-Keuls test) (42), $P<0.05$. Compound abbreviations as in FIG. 1.

EXAMPLE #7

In a 5-replicate experiment, a blend of 7R,8S-disparlure (10 µg), 7R,8S-epoxy-octadecane (10 µg) and 2-methyl-Z7-octadecene (1 µg) and a blend of racemic disparlure (20 µg), 7R,8S-epoxy-octadecane (10 µg), 7S,8R-epoxy-octadecane (10 µg) and 2-methyl-Z7-octadecene (1 µg) attracted on average 14.6 and 12.2 NM males, respectively (U-test, Mann-Whitney test), $P>0.05$). This difference in trap catches was statistically not significant, suggesting that chiral and racemic epoxides were equally effective in attracting NM.

*L. monacha* Pheromone Components Suppressed Cross-Attraction of *L. dispar* Males

EXAMPLE #1a

2-Methyl-Z7-octadecene and 7R,8S-epoxy-octadecane in combination enhanced attractiveness of RS-disparlure for NM males but reduced response of GM males (FIG. 7). Spruce forest near Zbraslav, Czech Republic, 2–4 Aug., 1995; 10 replicates. Bars in each horizontal row superscripted by the same letter are not significantly different; nonparametric analysis of variance by ranks (Friedman's test) followed by comparison of means (Student-Newman-Keuls test) (42), $P<0.05$. Compound abbreviations as in FIG. 1.

EXAMPLE #2a

Figure 8:
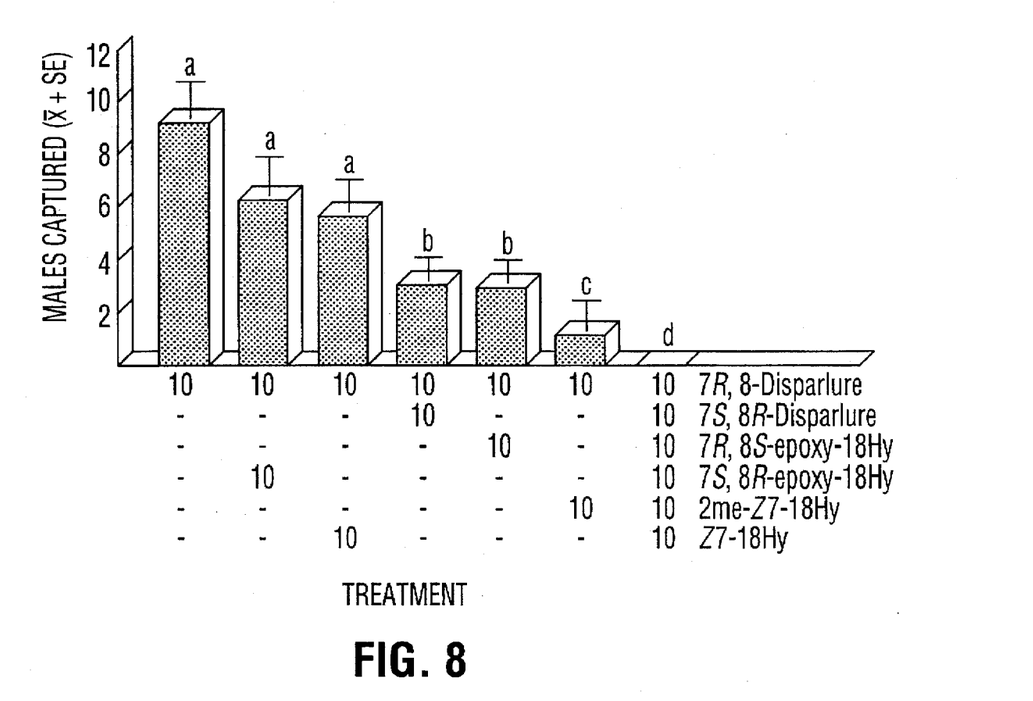
FIG. 8 illustrates graphical data of captures of *L. dispar* males in traps baited with 7R,8S-disparlure (10 µg) alone or in combination with either one or all of the following compounds at 10 µg each: 7S,8R-disparlure; 7R,8S-epoxy-18Hy; 7S,8R-epoxy-18Hy; 2me-Z7-18Hy; Z7-18Hy.

SR-Disparlure (10 µg), 7R,8S-epoxy-octadecane (10 µg) or 2-methyl-Z7-octadecene (10 µg) reduced attractiveness of 7R,8S-disparlure (10 µg), and all compounds combined (including 7S,8R-epoxy-octadecane and Z7-octadecene) completely suppressed attraction of GM males (FIG. 8). FIG. 8 illustrates graphical data of captures of *L. dispar* males in traps baited with 7R,8S-disparlure (10 µg) alone or in combination with either one or all of the following compounds at 10 µg each: 7S,8R-disparlure; 7R,8S-epoxy-18Hy; 7S,8R-epoxy-18Hy; 2me-Z7-18Hy; Z7-18Hy. Oak forest near Zbraslav, Czech Republic, 30–31 Jul., 1995; 10 replicates. Bars superscripted by the same letter are not significantly different; nonparametric analysis of variance by ranks (Friedman's test) followed by comparison of means (Student-Newman-Keuls test) (42), P<0.05. Compound abbreviations as in FIG. 1.

EXAMPLE #3a

Figure 9:
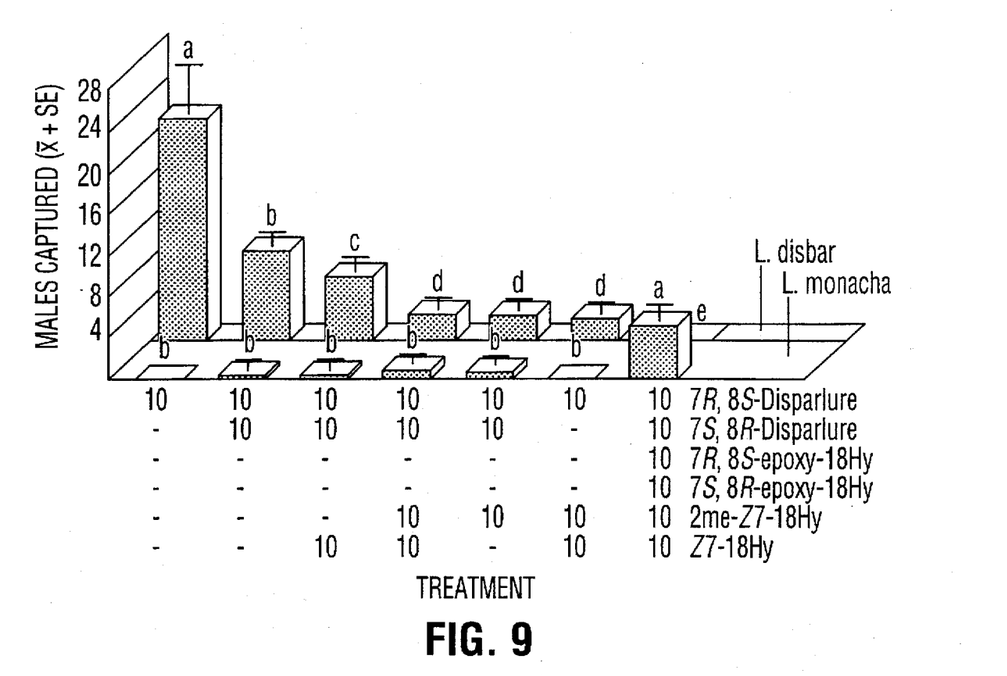
FIG. 9 illustrates graphical data of captures of *L. monacha* and *L. dispar* males in traps baited with 7R,8S-disparlure (10 µg) alone or in combination with one, two, three or all of the following compounds at 10 µg each: 7S,8R-disparlure; 7R,8S-epoxy-18Hy; 7S,8R-epoxy-18Hy; 2me-Z7-18Hy; Z7-18Hy.

In an oak forest, 7R,8S-disparlure by itself attracted a total of 172 (mean =21.5) GM males and 1 (mean=0.1) NM males, whereas a blend of NM pheromone components attracted no GM and 41 NM (mean=5.1) males (FIG. 9). FIG. 9 illustrates graphical data of captures of *L. monacha* and *L. dispar* males in traps baited with 7R,8S-disparlure (10 µg) alone or in combination with one, two, three or all of the following compounds at 10 µg each: 7S,8R-disparlure; 7R,8S-epoxy-18Hy; 7S,8R-epoxy-18Hy; 2me-Z7-18Hy; Z7-18Hy. Oak forest near Zbraslav, Czech Republic, 31 Jul., 1995; 8 replicates. Bars in each horizontal row superscripted by the same letter are not significantly different; nonparametric analysis of variance by ranks (Friedman's test) followed by comparison of means (Student-Newman-Keuls test) (42), P<0.05. Compound abbreviations as in FIG. 1.

Figure 10:
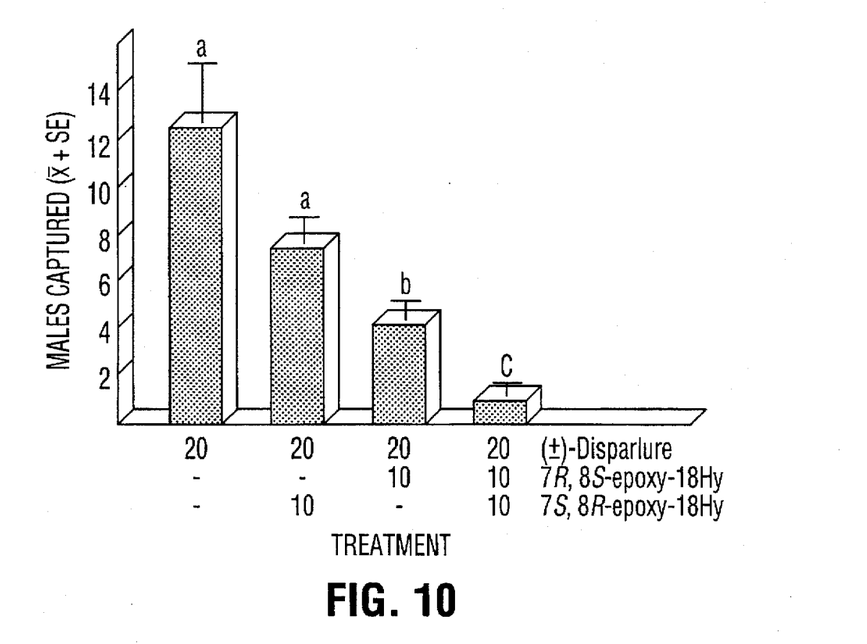
FIG. 10 illustrates graphical data of captures of *L. dispar* males in traps baited with (±) (7R,8S+7S,8R) disparlure (20 µg) alone and in binary combinations with 7R,8S-epoxy-18Hy (10 µg), 7S,8R-epoxy-18Hy (10 µg) or 7R,8S-epoxy-18Hy plus 7S,8R-epoxy-18Hy at 10 µg each.

EXAMPLE #4a 7R,8S-Epoxy-octadecane, the synergistic NM pheromone component, more strongly than its antipode reduced attraction of GM males to (±)-disparlure, but both enantiomers combined were significantly most effective (FIG. 10). FIG. 10 illustrates graphical data of captures of *L. dispar* males in traps baited with (±) (7R,8S+7S,8R)-disparlure (20 µg) alone and in binary combinations with 7R,8S-epoxy-18Hy (10 µg), 7S,8R-epoxy-18Hy (10 µg) or 7R,8S-epoxy-18Hy plus 7S,8R-epoxy-18Hy at 10 µg each. Oak forest near Zbraslav, Czech Republic, 4–5 Aug., 1995; 8 replicates. Bars superscripted by the same letter are not significantly different; ANOVA on data transformed by log 10 (x+1) followed by comparison of means (Student-Newman-Keuls test) (42), P<0.05. Compound abbreviations as in FIG. 1.

EXAMPLE #5a

Figure 11:
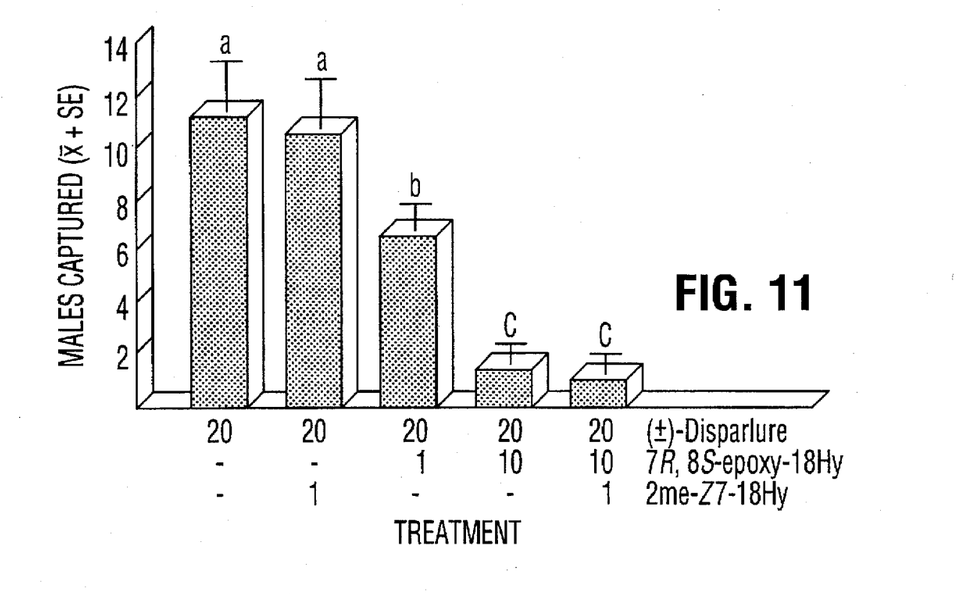
FIG. 11 illustrates graphical data of captures of *L. dispar* in traps baited with (±) (7R,8S+7S,8R)-disparlure (20 µg) alone and in binary or ternary combinations with 7R,8S-epoxy-18Hy (1 or 10 µg) and 2me-Z7-18Hy (1 µg).

The best blend for attraction of NM males (compare FIGS. 5 & 6) [7R,8S-disparlure (10 µg), 7R,8S-epoxy-octadecane (10 µg) and 2-methyl-Z7-octadecene (1 µg)] plus 10 µg of SR-disparlure (indifferent to NM; see example #7) were 10 times less attractive to GM males than RS- plus SR-(=racemic) disparlure (FIG. 11). FIG. 11 illustrates graphical data of captures of *L. dispar* in traps baited with (±) (7R,8S+7S,8R)-disparlure (20 µg) alone and in binary or ternary combinations with 7R,8S-epoxy-18Hy (1 or 10 µg) and 2me-Z7-18Hy (1 µg). Oak forest near Zbraslav, Czech Republic, 3 August, 1995; 8 replicates. Bars superscripted by the same letter are not significantly different; nonparametric analysis of variance by ranks (Friedman's test) followed by comparison of means (Student-Newman-Keuls test) (42), F<0.05. Ratio in the binary blend was based on results in FIG. 5. Compound abbreviations as in FIG. 1.

Figure 12:
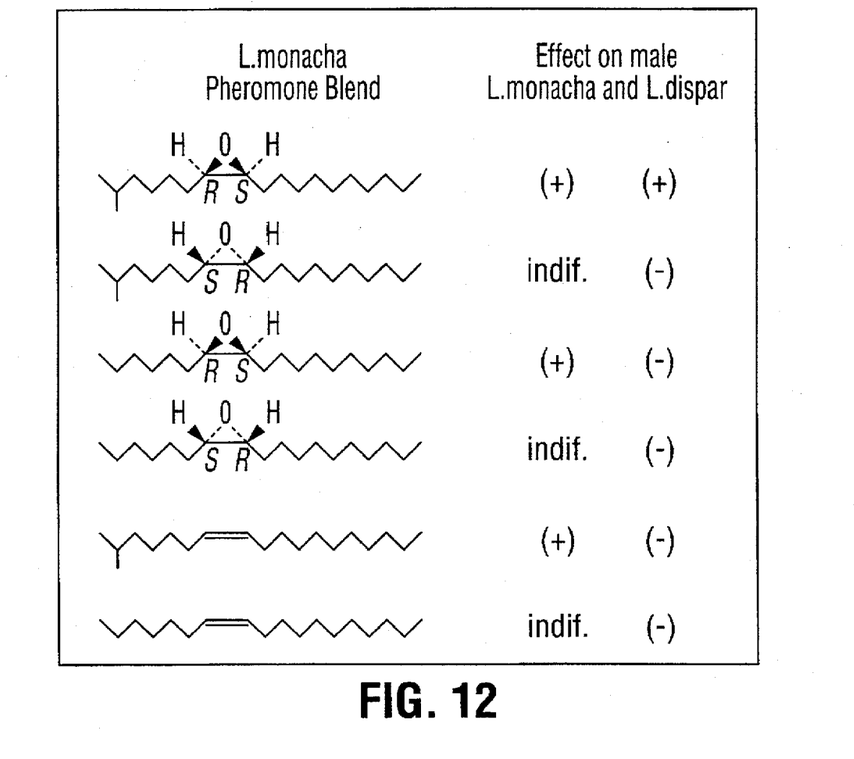
FIG. 12 illustrates graphical depictions of the components comprising the pheromone blend of *L. monacha* and their attractive (+), inhibitory (−) or indifferent (indif.) effect on *L. monacha* and *L. dispar* males.

Based on results presented in FIGS. 1–11, female NM produce a multiple component sex pheromone blend which attracts NM males significantly more strongly than 7R,8S-disparlure alone, and effectively suppresses cross-attraction of GM males (FIG. 12). FIG. 12 illustrates graphical depictions of the components comprising the pheromone blend of *L. monacha* and their attractive (+), inhibitory (−) or indifferent (indif.) effect on *L. monacha* and *L. dispar* males. All compounds may become part of a commercial lure (formulation) for manipulating, pheromone-based monitoring and/or control of NM and/or GM.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES AND NOTES

1. Jensen, T. S. & Nielsen, B. O. J. Appl. Entomol. 98, 399–413 (1984).
2. Schönherr, J. J. Appl. Entomol 99, 73–76 (1984).
3. Bejer, B. In Dynamics of forest insect populations: patterns, causes, implications (ed. Berryman, A.). Plenum Publ. Corp., New York, USA. 603 pp. (1988).
4. Grjpma, P. 1988. In Proceedings, Lymantriidae: a comparison of features of new and old world tussock moths (tech. coords. Wallner, W. E., McManus, K. A.). Dept. of Agr, Forest Service, Northeastern Forest Experiment Station, Gen. Tech. Rep. NE- 123. 554 pp. (1988).
5. Sliwa, E., Sierpinski, Z. Anz. Schädlingskde., Pflanzenschutz, Umweltschutz 59, 81–86 (1986).
6. Majunke, C., Haussler, D., Walter, C. Beitr. Forstwirts. 19, 89–91 (1985).
7. Wellenstein, G. & Schwenke, W. In Schwenke, W. The Forest pests of Europe. Parey VIII: 334–368 (1978).
8. Jkuhravy, V. Anz. Schädlingsk. Pflanzenschutz, Umweltschutz 60, 96–98.
9. Bierl, B. A., Beroza, M., Adler, V. E., Kasang, G., Schroter, H. & Schneider, D. Z. Naturforsch. 30c, 672–675 (1975).
10. Hochmut, R., Hrdy, I., Kolk, A., Liska, J., Rodziewicz, A., Vrkoc, J. & Zdarek, J. Lesnictvi 35, 535–548 (1989).
11. Skatulla, U. Anz. Schädlingskde., Pflanzenschutz, Umweltschutz 62, 50–53 (1989).
12. Jensen, T. S., Forest Ecol. and Manage. 39, 29–34 (1991).
13. Krehan, H. Forstschutz-Aktuell 14, 1–2 (1994)
14. Mason, R. R. In Proceedings, Lymantriidae: a comparision of features of new and old world tussock moths (tech. coords, Wallner, W. E., McManus, K. A.). Dept. of Agr. Forest Service, Northeastern Forest Experiment Station, Gen. Tech. Rep. NE- 123. 554 pp. (1988).
15. Jensen, T. S. Mitt. Dtsch. Ges. Alg. Angew. Entomol. 4, 146–149 (1984).
16. Zdarek, J., Vrokoc, J., Hochmut, R. & Kolk, A. J. Chem. Ecol. 14:537–547 (1988).
17. Bierl, B. A., Beroza, M. & Collier, C. M. Science 170, 87–89 (1970).
18. Bierl, B. A., Beroza, M. & Collier, C. M. J. Econ. Entomol. 65, 659–664 (1972).
19. Hansen, K., Physiol. Entomol. 9, 9–18 (1984).
20. Vité, J. P., Klimetzek, D., Loskant, G., Hedden, R. & Mori, K., Naturwissenschaften 63, 582–583 (1976).
21. Miller, J. R., Mori, K. & Roelofs, W. L. J. Insect Physiol. 23, 1447–1453 (1977).
22. Cardé, R. T., Doane, C. C., Granett, J., Hill, A. S., Kochansky, J. & Roelofs, W. L. Environ. Entomol. 6, 765–767 (1977).

23. Plimmer, J. R., Schwalbe, C. P., Paszek, E. C., Bierl, B. A., Webb, R. E., Marumo, S. & Iwaki, S. Environ. Entomol. 6, 518–522 (1977).
24. Cardé, R. T., Doane, C. C., Baker, T. C., Iwaki, S. & Marumo, S., Environ. Entomol. 6, 768–772 (1977).
25. Cardé, R. T., Roelofs, W. L. & Doane, C. C. Nature 241, 474–475 (1973).
26. Grant et al., unpublished.
27. Liska et al., unpublished.
28. Bierl, B. A. a Beroza, M. Methods of increasing the attraction of the gypsy moth, *Porthetria dispar*. U.S. Pat. No. 3,876,772 (1975).
29. Kupper, F. -W. & Streck, R. Process for the preparation of 7,8-epoxy-2-methyloctadecane. U.S. Pat. No. 4,036,858 (1977).
30. Eiter, K. Preparation of cis-7,8-epoxy-2-methyloctadecane. U.S. Pat. No. 3,975,409 (1976).
31. Leonhardt, B. A., DeVilbiss, E. D. & Mastro, V. C. PVC/twine dispenser for (+)-disparlure. U.S. Pat. No. 5,324,618 (1994).
32. Payne, C. C. Sprayable adhesive for gypsy moth pheromone beads. U.S. Pat. No. 5,324,517 (1994).
33. Briese, M. W. Insect trap for gypsy moth and other flying insects. U.S. Pat. No. 5,133,150 (1992).
34. Seidenberger, J. W. Method and apparatus for trapping flying insects exhibiting phototropic behaviour, particularly gypsy moth. U.S. Pat. No. 4,400,903 (1983).
35. Browne, L. E. Method and apparatus for forming a collapsible trap for flying insects. U.S. Pat. No. 4,442,624 (1984).
36. Kuchenbecker, M. W. Gypsy moth trap. U.S. Pat. No. 3,885,341 (1975).
37. Gas chromatographic (GC) or GC-electroantennographic (EAD) analyses employed a Hewlett Packard 5890B gas chromatograph equipped with a fused silica column (30 m×0.25 or 0.32 mm ID) coated with DB-210, DB-23 or DB-5 (J & W Scientific, Folsom, Calif.).
38. A detailed description of synthetic procedures and complete chemical characterizations of all compounds field tested will be given elsewhere.
39. Arn, H., Städler, E. & Rauscher, S. Z. Naturforsch. 30c, 722–725 (1975).
40. Delta traps consisted of a delta-shaped 2-liter plasticized milk carton prepared by RG and GG. The inner 855 $cm^2$ surface was covered with adhesive tangle—Trap (Tanglefoot Company, Grand Rapid, Minn.) to retain moths approaching the chemical lure in the middle of the trap.
41. Grey sleeve stoppers (West Company, Phoenixville, Pa.) served as release device.
42. SAS/STAT User's guide, 1988, release 6.04 edition, SAS inst. inc., Cary, N.C., 27513.

We claim:

1. A composition of chemicals for manipulating the behavior of nun moth and/or gypsy moth, said composition comprising:

2-methyl-7R,8S-epoxy-octadecane (RS-disparlure);
2-methyl-7S,8R-epoxy-octadecane (SR-disparlure);
and 2-methyl-Z7-octadecene, plus at least about 10 percent weight of one or more chemicals selected from the group consisting of:
  (a) 7R,8S-epoxy-octadecane;
  (b) 7S,8R-epoxy-octadecane;
  and
  (c) Z7-octadecene.

2. A composition as claimed in claim 1 wherein the chemicals comprise 2-methyl-7R,8S-epoxy-octadecane, 2-methyl-7S,8R-epoxy-octadecane, 2-methyl-Z7-octadecene and 7R,8S-epoxy-octadecane.

3. A composition as claimed in claim 1 wherein the chemicals comprise 2-methyl-7R,8S-epoxy-octadecane, 2-methyl-7S,8R-epoxy-octadecane, 2-methyl-Z7-octadecene, and 7S,8R-epoxy-octadecane.

4. A composition as claimed in claim 1 wherein the chemicals comprise 2-methyl-7R,8S-epoxy-octadecane, 2-methyl-7S,8R-epoxy-octadecane, 2-methyl-Z7-octadecene and Z7-octadecene.

5. A composition as claimed in claim 1 wherein the chemicals comprise 7R,8S-disparlure, 7S,8R-disparlure, 2-methyl-Z7-octadecene, 7R,8S-epoxy-octadecane and 7S,8R-epoxy-octadecane.

6. A composition as claimed in claim 1 wherein the chemicals comprise 7R,8S-disparlure, 7S,8R-disparlure, 7R,8S-epoxy-octadecane, 2-methyl-Z7-octadecene, and Z7-octadecene.

7. A composition as claimed in claim 1 wherein the chemicals comprise 7R,8S-disparlure, 7S,8R-disparlure, 7S,8R-epoxy-octadecane, 2-methyl-Z7-octadecene and Z7-octadecene.

8. A composition as claimed in claim 1 wherein the chemicals comprise 7R,8S-disparlure, 7S,8R-disparlure, 7R,8S-epoxy-octadecane, 7S,8R-epoxy-octadecane, 2-methyl-Z7-octadecene and Z7-octadecene.

9. A composition as claimed in claim 1 wherein the composition is contained in, and released from, a trap that captures attracted nun moths or gypsy moths.

10. A composition as claimed in claim 1 wherein the chemicals are contained in, and released from, slow release devices.

11. A method of capturing nun moths and gypsy moths which comprises baiting a trap with two or more chemicals as claimed in claim 1.

12. A method as claimed in claim 11 wherein the chemicals as claimed in claim 1 are held in a slow release device.

13. A composition of chemicals for manipulating the behavior of nun moth and/or gypsy moth, said composition comprising the following chemicals:
  (a) 10 parts 2-methyl-7R,8S-epoxy-octadecane;
  (b) 10 parts 2-methyl-7S,8R-epoxy-octadecane;
  (c) 10 parts 7R,8S-epoxy-octadecane;
  (d) 10 parts 7S,8R-epoxy-octadecane; and
  (e) 1 part 2-methyl-Z7-octadecene.

14. A composition as claimed in claim 5 wherein there are 10 parts each 7R,8S-disparlure, 7S,8R-disparlure, 7R,8S-epoxy-octadecane, 7S,8R-epoxy-octadecane and 1 part 2-methyl-Z7-octadecene.

* * * * *